(12) United States Patent
Bonnert et al.

(10) Patent No.: US 6,958,343 B2
(45) Date of Patent: Oct. 25, 2005

(54) THIAZOLOPYRIMIDINES AND THEIR USE AS MODULATORS OF CHEMOKINE RECEPTOR ACTIVITY

(75) Inventors: Roger Bonnert, Loughborough (GB); Peter Cage, Loughborough (GB); Fraser Hunt, Loughborough (GB); Robert Jewell, Loughborough (GB); Iain Walters, Loughborough (GB)

(73) Assignee: AstraZeneca, AB, Södertälje (SE)

( * ) Notice: Subject to any disclaimer, the term of this patent is extended or adjusted under 35 U.S.C. 154(b) by 0 days.

(21) Appl. No.: 10/203,580

(22) PCT Filed: Feb. 7, 2001

(86) PCT No.: PCT/SE01/00247

§ 371 (c)(1),
(2), (4) Date: Aug. 9, 2002

(87) PCT Pub. No.: WO01/58907

PCT Pub. Date: Aug. 16, 2001

(65) Prior Publication Data

US 2003/0032642 A1 Feb. 13, 2003

(30) Foreign Application Priority Data

Feb. 11, 2000 (GB) .............................. 0003025

(51) Int. Cl.[7] ..................... C07D 513/04; A61K 31/519
(52) U.S. Cl. .................................. 514/260.1; 544/255
(58) Field of Search ........................ 514/260.1; 544/255

(56) References Cited

U.S. PATENT DOCUMENTS

| | | |
|---|---|---|
| 2,924,472 A | 2/1960 | Bush |
| 3,318,900 A | 5/1967 | Janssen |
| 3,445,120 A | 5/1969 | Barr |
| 4,061,459 A | 12/1977 | Parmann |
| 4,126,689 A | 11/1978 | Sanczuk et al. |
| 4,188,040 A | 2/1980 | Wolf et al. |
| 4,213,619 A | 7/1980 | Arlt et al. |
| 4,234,199 A | 11/1980 | Moncaster et al. |
| 4,278,677 A | 7/1981 | Nedelec et al. |
| 4,410,528 A | 10/1983 | Teranishi et al. |
| 4,483,544 A | 11/1984 | Faerber et al. |
| 4,641,858 A | 2/1987 | Roux |
| 5,064,207 A | 11/1991 | Bengtsson |
| 5,169,161 A | 12/1992 | Jones |
| 5,297,824 A | 3/1994 | Imhof et al. |
| 5,521,197 A | 5/1996 | Audia |
| 5,599,028 A | 2/1997 | Neumann et al. |
| 5,988,695 A | 11/1999 | Corbett, Jr. |
| 6,142,484 A | 11/2000 | Valls, Jr. |
| 6,172,067 B1 | 1/2001 | Ito et al. |
| 6,248,755 B1 | 6/2001 | Chapman et al. |
| 6,329,381 B1 | 12/2001 | Kurimoto et al. |
| 6,407,121 B1 | 6/2002 | Nagamine et al. |
| 6,432,981 B1 | 8/2002 | Finke et al. |
| 2003/0176693 A1 | 9/2003 | Tsushima et al. |

FOREIGN PATENT DOCUMENTS

| | | |
|---|---|---|
| DE | 2331223 | 1/1974 |
| DE | 41 19 767 A1 | 12/1992 |
| EP | 0 293 078 A1 | 11/1988 |
| EP | 0 447 324 A1 | 9/1991 |
| EP | 0778277 A1 | 6/1997 |
| EP | 1 069 124 B1 | 1/2001 |
| EP | 1 122 257 A1 | 8/2001 |
| GB | 2359079 A | 8/2001 |
| JP | 51-88994 | 8/1976 |
| WO | WO 97/40035 | 10/1997 |
| WO | WO 98/08847 | 3/1998 |
| WO | WO 98/25617 | 6/1998 |
| WO | WO 99/04794 | 2/1999 |
| WO | WO 99/17773 | 4/1999 |
| WO | WO 99/36421 | 7/1999 |
| WO | WO99/51608 | 10/1999 |
| WO | WO 00/08013 | 2/2000 |
| WO | WO 00/09511 A1 | 2/2000 |
| WO | WO 00/38680 | 7/2000 |
| WO | WO 00/39129 | 7/2000 |
| WO | WO 00/45800 | 8/2000 |
| WO | WO 00/59502 | 10/2000 |
| WO | WO 00/76514 | 12/2000 |
| WO | WO 01/19825 | 3/2001 |
| WO | WO 01/25200 | 4/2001 |
| WO | WO 01/25242 A1 | 4/2001 |
| WO | WO 01/25242 | 4/2001 |
| WO | WO 01/58902 | 8/2001 |
| WO | WO 01/58906 | 8/2001 |
| WO | WO 01/62758 | 8/2001 |
| WO | WO 01/6525 | 9/2001 |
| WO | WO 02/083693 | 10/2002 |
| WO | WO 03/024966 | 3/2003 |

OTHER PUBLICATIONS

Trivedi, B.K. et al, Ann. Reports Med. Chem., vol. 35, 2000, pp. 191–200.*

(Continued)

Primary Examiner—Thomas C. McKenzie
(74) Attorney, Agent, or Firm—Fish & Richardson, P.C.

(57) ABSTRACT

Compounds of formula (I):

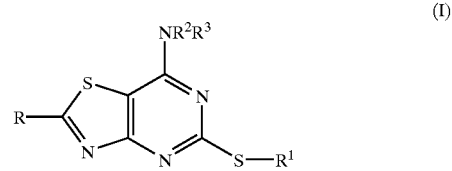

are described herein. The compounds can be used, for example, in the treatment of chemokine mediated diseases, including inflammatory diseases such as psoriasis and COPD.

8 Claims, No Drawings

OTHER PUBLICATIONS

West, Anthony R., "Solid State Chemistry and its Applications," Wiley, New York, 1988, pp. 358 & 365.*

STN International, file CAPLUS, CAPLUS accession No. 1996: 243961, document No. 125: 10744, Gewald, K. et al.: "New Synthesis of substituted 4–aminoquinazolines and their hetero analogs", J. Prakt. Chem./Chem.–Ztg.,338 (3) 206–213 (1996).

Ahmed et al., "Novel synthesis of 1–aryl–9–alkyl–2,3,3a,4, 9,9a–hexahydro–1H–pyrrolo[2,3–b]quinoxalines by lithium aluminum hydride reduction of N–phenyl–1–benzimidazolylsuccinimides", CAPLUS 79:92106 (1973).

Chemical Abstracs, vol. 54, No. 10, May 1960, Abstract No. 9933f, C. Wayne Noell and Roland K. Robins, "Potential Purine Antagonists XVII. Synthesis of 2–methyl and 2–methylthio–6, 8–disubstituted purines", see formula III when R–SMe,R1=Cl, R2=OH.

Cohen et al., "Cytokine function: A study in biologic diversity", CAPLUS 125:31527 (1996).

Cowley et al., "Preparation of 1–(3–phenyloxypropyl)piperdine derivatives as opioid receptor ligands", CAPLUS 138:39189 (2002).

Finke et al., "Preparation of pipeidinylmethylcyclopentanes as modulators of CCR–5 and/or CCR–3 chemokine receptors", CAPLUS 134:56576 (2000) CAS Listing, 77 answers.

Fukuda et al., "Preparation of benzotriazole derivatives as cardiovascular agents and antipsychotics", CAPLUS 123:340149 (1995).

Grant, "University of Minnesota–Twin Cities Campus College of Pharmacy, Annual Report", [online] 1999, [retrieve on Feb. 13, 2003]. Retrieved from the internet, http://www.msl.umn.edu/general/Reports/ar99/departments/pharmacy.html.

Kiriasis et al., "Synthesis and Properties of New Pteridine Nucleosides", *Dev. Biochem.* 4:49–53 (1978).

McNaught et al., "IUPAC Compendium of Chemical Terminology, $2^{nd}$ Ed" (1997).

Ottetal.,"4–amino–7,8–dihydro–2–(methylmercapto)–8–β,–D–ribofuranosylpteridin–7–One. Modified Fusion Reaction with Trimethylsilylated Pteridine Derivatives", *Nucl. Acid. Chem.* 2:735–739 (1978).

Ott et al., "Zur Synthese des 4–Amino–7–oxo–7, 8–dihydropteridin–N–8–β–D–ribofuranosids—ein strukturanaloges Nucleosid des Adenosins", *Chem. Ber.* 107:339–361 (1974).

Patents Abstracts of Japan, abstract of JP–5–202047 A (Chugai Pharmaceut. Co. Ltd.) Aug. 10, 1993.

Sato et al., "Psychotropic agents, 3, 4–(4–Substituted piperidinyl)–1–(4–flurophenyl)–1–butanones with potent neuroleptic activity", CAPLUS 89:208915 (1978).

Sato et al., "Psychotropic Agents. $3.^1$4–(4–Substituted piperidinyl)–1–(4–flurophenyl)–1–butanones with Potent Neuroleptic Activity," *Journal of Medicinal Chemistry* 21(11):1116–1120 (1978).

Taylor et al., "Molecular Determinants for Recognition of RU 24969 Analogs at Central 5–Hydroxytryptamine Recognition Sites: Use of a Bilinear Function and Substituent Volumes to Describe Steric Fit," *Molecular Pharmacology* 32:42–53 (1988).

Teranishi et al., "Piperidine derivatives and pharmaceutical compositions containing them", CAPLUS 95:132947 (1981).

Vandenberk et al., "1–(Benzazolylalkyl)piperidines and their salts with acids", CAPLUS 87:23274 (1977).

Vartanyan et al., "Synthesis and biological activity of 1–substituted benzimidazole and benztriazole derivatives", CAPLUS 98:4503 (1983).

* cited by examiner

THIAZOLOPYRIMIDINES AND THEIR USE AS MODULATORS OF CHEMOKINE RECEPTOR ACTIVITY

CROSS REFERENCE TO RELATED APPLICATIONS

The present application is a national phase application under 35 U.S.C. Section 371 filed from International Patent Application PCT/SE01/00247, filed 7 Feb. 2001, which claims priority to United Kingdom patent application Serial. No. 0003025.4, filed 11 Feb. 2000. The contents of these applications are incorporated herein by reference in their entirety.

The present invention relates to certain thiazolopyrimidine compounds, processes and intermediates used in their preparation, pharmaceutical compositions containing them and their use in therapy.

The compound 2,7-diamino-5-methylmercapto-thiazolo[4,5-d]pyrimidine is known from J. Amer. Chem. Soc., 73, 4226–4227 (1951).

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. At the present time, the chemokine superfamily comprises three groups exhibiting characteristic structural motifs, the C—X—C, C—C and C—X$_3$—C families. The C—X—C and C—C families have sequence similarity and are distinguished from one another on the basis of a single amino acid insertion between the NH-proximal pair of cysteine residues. The C—X$_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

The C—X$_3$—C chemokine (also known as fractalkine) is a potent chemoattractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and CX$_3$CR1 for the C—X$_3$—C family. These receptors represent good targets for drug development since agents which modulate these receptors would be useful in the treatment of disorders and diseases such as those mentioned above.

In accordance with the present invention, there is therefore provided compounds of formula (I) or a pharmaceutically acceptable salts or solvates thereof:

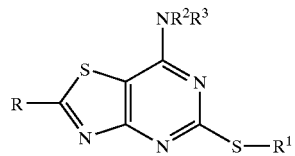

(I)

wherein R represents a hydrogen atom, or a group —NR$^4$R$^5$;
R$^4$ and R$^5$ each independently represent a hydrogen atom, or a 4-piperidinyl, C$_3$–C$_6$ cycloalkyl or C$_1$–C$_8$ alkyl group, which latter two groups may be optionally substituted by one or more substituent groups independently selected from halogen atoms and —NR$^6$R$^7$, —CONR$^6$R$^7$, —OR$^8$, —COOR$^8$, —NR$^9$COR$^{10}$, —SR$^{11}$, —SO$_2$R$^{11}$, —SO$_2$NR$^6$R$^7$, —NR$^9$SO$_2$R$^{10}$, morpholinyl, C$_1$–C$_4$ alkyl, C$_3$–C$_6$ cycloalkyl, tetrahydrofuranyl, aryl and heteroaryl groups, the aryl and heteroaryl groups being optionally substituted by one or more substituents independently selected from halogen atoms and cyano, nitro, —NR$^6$R$^7$, —CONR$^6$R$^7$, —OR$^8$, —NR$^9$COR$^{10}$, —SO$_2$NR$^6$R$^7$, —NR$^9$SO$_2$R$^{10}$, C$_1$–C$_6$ alkyl and trifluoromethyl groups,
or R$^4$ and R$^5$ together with the nitrogen atom to which they are attached form a 4- to 7-membered saturated heterocyclic ring system, which ring system may be optionally substituted by one or more substituent groups independently selected from

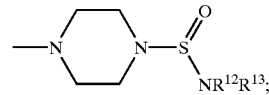

—NR$^6$R$^7$, —CONR$^6$R$^7$, —OR$^8$, —COOR$^8$, —NR$^9$COR$^{10}$, and C$_1$–C$_6$ alkyl optionally substituted by one or more substituents independently selected from halogen atoms and —NR$^{11}$R$^{12}$ and —OR$^8$ groups,
R$^1$ represents a C$_1$–C$_6$ alkyl group substituted by a five-membered heterocycle;
R$^2$ and R$^3$ each independently represent a hydrogen atom, or a C$_3$–C$_7$ carbocyclic, C$_1$–C$_8$ alkyl, C$_2$–C$_6$ alkenyl or C$_2$–C$_6$ alkynyl group, the latter four groups may be optionally substituted by one or more substituent groups independently selected from:
halogen atoms, —NR$^6$R$^7$, —CONR$^6$R$^7$, —OR$^8$, —COOR$^8$, —NR$^9$COR$^{10}$, —SR$^{11}$, —SO$_2$R$^{11}$, —SO$_2$NR$^6$R$^7$, —NR$^9$SO$_2$R$^{10}$
or
a 3–8 membered ring optionally containing one or more atoms selected from O, S, NR$^9$ and itself optionally substituted by C$_{1-3}$-alkyl, halogen,
R$^8$ represents hydrogen, C$_1$–C$_6$ alkyl or a phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$
R$^6$ and R$^7$ independently represent a hydrogen atom or a C$_1$–C$_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$
or
R$^6$ and R$^7$ together with the nitrogen atom to which they are attached form a 4- to 7-membered saturated heterocyclic ring system optionally comprising a further heteroatom selected from oxygen and nitrogen atoms, which ring system may be optionally substituted by one or more substituent groups independently selected from phenyl, —OR$^4$, —COOR$^{14}$, —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or C$_1$–C$_6$ alkly, itself optionally substituted by one or more substituents independently selected from halogen atoms and —NR$^{15}$R$^{16}$ and —OR$^{17}$ groups, R$^{11}$ represents a hydrogen atom or a C$_1$–C$_6$, or phenyl group, each of which may be optionally substituted by one or more substituent groups independently selected from halogen atoms, phenyl, —OR$^{17}$ and —NR$^{15}$R$^{16}$, and R$^9$, R$^{10}$, R$^{12}$, R$^{13}$, R$^{14}$ R$^{15}$, R$^{16}$, and R$^{17}$ independently represent a hydrogen atom or a C$_1$–C$_6$, alkyl, or a phenyl group.

In the context of the present specification, unless otherwise indicated, an alkyl or alkenyl group or an alkyl or alkenyl moiety in a substituent group may be linear or branched.

Aryl groups include phenyl and naphthyl. Heteroaryl is defined as a 5- or 6-membered aromatic ring optionally containing one or more heteroatoms selected from N, S, O. Examples include pyridine, pyrimidine, thiazole, oxazole, pyrazole, imidazole, furan. Heterocyclic rings as defined for R$^4$ and R$^5$ means saturated heterocycles, examples of which include morpholine azetidine, pyrrolidine, piperidine and piperazine.

In formula (I) above, the group R represents a hydrogen atom, or a group —NR$^4$R$^5$. Particularly advantageous compounds of formula (I) are those in which R represents a group —NR$^4$R$^5$.

Suitably R$^4$ and R$^5$ each independently represent a hydrogen atom, or a 4-piperidinyl, C$_3$–C$_6$ cycloalkyl or C$_1$–C$_8$ alkyl group, which latter two groups may be optionally substituted by one or more substituent groups independently selected from halogen atoms and —NR$^6$R$^7$, —CONR$^6$R$^7$, —OR$^8$, —COOR$^8$, —NR$^9$COR$^{10}$, —SR$^{11}$, —SO$_2$R$^{11}$, —SO$_2$NR$^6$R$^7$, —NR$^9$SO$_2$R$^{10}$, morpholinyl, C$_1$–C$_4$ alkyl, C$_3$–C$_6$ cycloalkyl, tetrahydrofuranyl, aryl and heteroaryl groups, each of which may be optionally substituted by one or more substituents independently selected from halogen atoms and cyano, nitro, —NR$^6$R$^7$, —CONR$^6$R$^7$, —OR$^8$, —NR$^9$COR$^{10}$, —SO$_2$NR$^6$R$^7$, NR$^9$SO$_2$R$^{10}$, C$_1$–C$_6$ alkyl and trifluoromethyl groups, or R$^4$ and R$^5$ together with the nitrogen atom to which they are attached form a 4- to 7-membered saturated heterocyclic ring system, which ring system may be optionally substituted by one or more substituent groups independently selected from

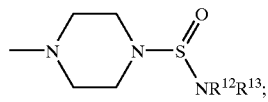

—NR$^6$R$^7$, —CONR$^6$R$^7$, —OR$^8$, —COOR$^8$, —NR$^9$COR$^{10}$, and C$_1$–C$_6$ alkyl optionally substituted by one or more substituents independently selected from halogen atoms and —NR$^{11}$R$^{12}$ and —OR$^8$ groups.

Particularly advantageous compounds of formula (I) are those in which R$^4$ and R$^5$ each independently represent a hydrogen atom, or a C$_1$–C$_6$ alkyl group substituted by a —CONR$^5$R$^6$ or imidazolyl (e.g. 1H-imidazol-4-yl) group.

Suitably R$^1$ represents a methyl group substituted by furan or thiazole,.

Suitably R$^2$ and R$^3$ each independently represent a hydrogen atom, or a C$_3$–C$_7$ carbocyclic, C$_1$–C$_8$ alkyl, C$_2$–C$_6$ alkenyl or C$_2$–C$_6$ alkynyl group, the latter four groups may be optionally substituted by one or more substituent groups independently selected from:

halogen atoms, —NR$^6$R$^7$, —CONR$^6$R$^7$, —OR$^8$, —COOR$^8$, —NR$^9$COR$^{10}$, —SR$^{11}$, —SO$_2$R$^{11}$, SO$_2$NR$^6$R$^7$, —NR$^9$SO$_2$R$^{10}$ or a 3–8 membered ring optionally containing one or more atoms selected from O, S, NR$^9$ and itself optionally substituted by C$_{1-3}$-alkyl, halogen.

Preferably one of R$^2$ and R$^3$ is hydrogen and the other is C$_1$–C$_8$ alkyl substituted by hydroxy and one or more methyl or ethyl groups. More preferably one of R$^2$ and R$^3$ is hydrogen and the other is CH(CH$_3$)CH$_2$OH, CH(Et)CH$_2$OH, C(CH$_3$)$_2$CH$_2$OH or CH(CH$_2$OH)$_2$. When one of R$^2$ and R$^3$ is hydrogen and the other is CH(CH$_3$)CH$_2$OH or CH(Et)CH$_2$OH the resulting compounds of formula (I) are preferably in the form of the (R) isomer. Most preferably one of R$^2$ and R$^3$ is hydrogen and the other is CH(CH$_3$)CH$_2$OH.

Particularly preferred compounds of the invention include:

2-[[2-Amino-5-[(1H-benzimidazol-2-ylmethyl)thio]thiazolo[4,5-d]pyrimidin-7-yl]amino]-2-methyl-1-propanol 2-[[2-Amino-5-[(2-furanylmethyl)thio]thiazolo[4,5-d]pyrimidin-7-yl]amino]-2-methyl-1-propanol 2-[[2-Amino-5-[[1-(2-thienyl)ethyl]thio]thiazolo[4,5-d]pyrimidin-7-yl]amino]-2-methyl-1-propanol (2R)-2-[[2-Amino-5-[[(2-methyl-4-thiazolyl)methyl]thio]thiazolo[4,5-d]pyrimidin-7-yl]amino]-1-propanol (2R)-2-[[2-Amino-5-[[(3,5-dimethyl-4-isoxazolyl)methyl]thio]thiazolo[4,5-d]pyrimidin-7-yl]amino]-1-propanol (2R)-2-[[2-Amino-5-[[(5-methyl-2-furanyl)methyl]thio]thiazolo[4,5-d]pyrimidin-7-yl]amino]-1-propanol N-[4-[[[2-Amino-7-[[(1R)-2-hydroxy-1-methylethyl]amino]thiazolo[4,5-d]pyrimidin-5-yl]thio]methyl]-2-thiazolyl]-acetamide, (2R)-2-[[2-Amino-5-[[(5-chloro-1,2,3-thiadiazol-4-yl)methyl]thio]thiazolo[4,5-d]pyrimidin-7-yl]amino]-1-propanol (2R)-2-[[2-Amino-5-[(5-isoxazolylmethyl)thio]thiazolo[4,5-d]pyrimidin-7-yl]amino]-1-propanol 2-[[2-Amino-5-[[(2-methyl-4-thiazolyl)methyl]thio]thiazolo[4,5-d]pyrimidin-7-yl]amino]-1,3-propanediol 2-[[2-Amino-5-[[(2-methyl-4-thiazolyl)methyl]thio]thiazolo[4,5-d]pyrimidin-7-yl]amino]-2-methyl-1-propanol (2R)-2-[[2-Amino-5-[(2-furanylmethyl)thio]thiazolo[4,5-d]pyrimidin-7-yl]amino]-1-propanol and their pharmaceutically acceptable salts and solvates.

According to the invention there is also provided a process for the preparation of a compound of formula (I) which comprises:

a) treatment of a compound of formula (II):

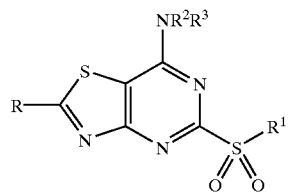

(II)

where R, R$^1$, R$^2$ and R$^3$ are as defined in formula (I) or are protected derivatives thereof with a thiol R$^1$SH in the presence of a base, or (b) treatment of a compound of formula (III):

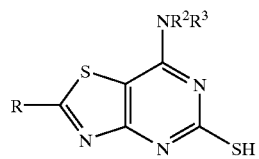

(III)

where R, $R^2$ and $R^3$ are as defined in formula (I) or are protected derivatives thereof with a compound of formula $R^1X$ where $R^1$ is as defined in formula (I) and X is a leaving group, and optionally after (a) or (b):

removing any protecting groups;

forming a pharmaceutically acceptable salt or solvate.

Reaction (a) may be carried out in a solvent such as DMSO at a temperature between 0° C. and 100° C. using a base such as potassium tert-butoxide.

Reaction (b) may be carried out in NMP at room temperature. The leaving group X is preferably halogen such as bromide. Preferbly the reaction is carried out in the presence of a base such as N,N-diisopropylethylamine. The reaction may be carried out in a suitable solvent such as NMP at room temperature.

Compounds of formula (II) where $R^1$, $R^2$ and $R^3$ are as defined in formula (I) may be prepared by treatment of a compound of formula (IV):

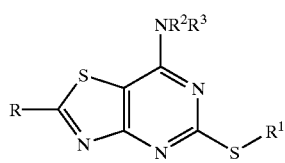

(IV)

where R, $R^1$, $R^2$ and $R^3$ are as defined above with an oxidizing agent such as peracetic acid. The reaction may be carried out in a solvent such as glacial acetic acid at a temperature between 0° C. and 100° C.

Compounds of formula (III) where R, $R^2$ and $R^3$ are as defined in formula (I) may be prepared by treatment of a compound of formula (IV) where R, $R^1$, $R^2$ and $R^3$ are as defined in formula (I) with sodium in liquid ammonia.

Compounds of formula (IV) where R, $R^1$, $R^2$ and $R^3$ are as defined in formula (I) may be prepared by treatment of a compound of formula (V) where R and $R^1$ is as defined above and L is a halogen such as chlorine with an amine $HNR_2R_3$. The reaction may be carried out in a solvent such as tetrahydrofuran in a sealed vessel at a temperature between 0° C. and 150° C.

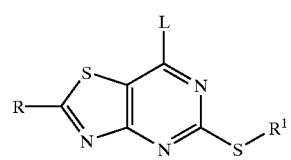

(V)

Compounds of formula (V) where R and $R^1$ are as defined in formula (I) and L is a halogen may be prepared by treating a compound of formula (V) where R and $R^1$ are as defined in formula (I) and L is a hydroxyl group with a halogenating agent such as phosphorous oxychloride. The reaction may be carried out at reflux in the presence of dimethylaniline.

Compounds of formula (V) where R=NH2 and $R^1$ is as defined in formula (I) and L is a hydroxyl group may be formed by heating a compound of formula (VI) where $R^1$ is as defined above.

Compounds of formula (V) where R and $R^1$ is defined in formula (I) and L is a halogen can be prepared from compounds of formula (V) where R is a halogen and $R^1$ is defined above with an amine $NR^4R^5$. The reaction may be carried out in a solvent such as tetrahydrofuran in a sealed vessel at a temperature between 0° C. and 150° C.

Compounds of formula (V) where R is a halogen, $R^1$ is defined in formula (I) and L is a halogen can be prepared from compounds of formula (V) where R is $NH_2$ and $R^1$ and L are defined above with a diazotizing agent and a halogenating agent. This process is conveniently carried out in an organic solvent such as acetonitrile in the presence of a diazotizing agent such as tert-butyl nitrite and a halogenating agent such as a trimethylsilyl halide.

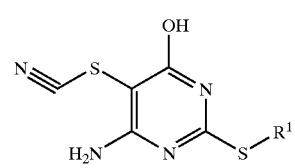

(VI)

Compounds of formula (VI) where $R^1$ is as defined in formula (I) may be readily prepared by reacting a compound of general formula (VII) wherein $R^1$ is as defined above, with potassium thiocyanate and bromine in an inert solvent such as dimethylformamide/pyridine.

Componds of formula (V) where R=NH2 and $R^1$ is defined in formula (I) and L is a hydroxyl group may also be prepared from compounds od general formula (VII) without isolation of imtermediate (VI).

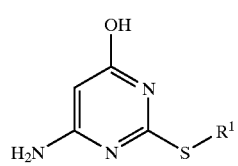

(VII)

Compounds of formula (VII) are suitably prepared by reacting a compound of formula (VIII):

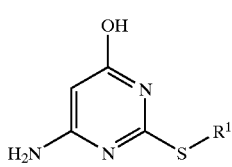

(VIII)

with a compound of formula $R^1X$ where $R^1$ is as defined above and X is a leaving group such as bromide in the presence of a base such as sodium hydroxide.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

Novel intermediate compounds form a further aspect of the invention. In particular compounds of formula (II) and (III) are novel and form an aspect of the invention.

The compounds of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

The compounds of formula (I) have activity as pharmaceuticals, in particular as modulators of chemokine receptor (especially CXCR2) activity, and may be used in the treatment (therapeutic or prophylactic) of conditions/diseases in human and non-human animals which are exacerbated or caused by excessive or unregulated production of chemokines.

Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyperresponsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal diorders, e.g. tropical spastic paraparesis, and stiff-man syndrome: paraneoplastic syndromes, e.g. cerebellar degeneration and encephalomyelitis; CNS trauma; migraine; and stroke.

(6) (other tissues and systemic disease) atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) (allograft rejection) acute and chronic following, for example, transplantation of kidney, heart, liver, lung, bone marrow, skin and cornea; and chronic graft versus host disease;

(8) Cancers, especially non-small cell lung cancer (NSCLC), malignant melanoma, prostate cancer and squamous sarcoma, and tumour metastasis;

(9) Diseases in which angiogenesis is associated with raised CXCR2 chemokine levels (e.g. NSCLC, diabetic retinopathy).

(10) Cystic fibrosis, re-perfusion injury in the heart, brain, peripheral limbs and other organs.

(11) Burn wounds & chronic skin ulcers

(12) Reproductive Diseases (e.g. Disorders of ovulation, menstruation and implantation, Pre-term labour, Endometriosis)

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CXC chemokine receptor subfamily, more preferably the target chemokine receptor is the CXCR2 receptor, Particular conditions which can be treated with the compounds of the invention are psoriasis, diseases in which angiogenesis is associated with raised CXCR2 chemokine levels, and COPD. It is preferred that the compounds of the invention are used to treat psoriasis.

As a further aspect of the present invention, certain compounds of formula (I) may have utility as antagonists of the CX3CR1 receptor. Such compounds are expected to be particularly useful in the treatment of disorders within the central and peripheral nervous system and other conditions characterized by an activation of microglia and/or infiltration of leukocytes (e.g. stroke/ischemia and head trauma).

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula (I), or a pharmaceutically acceptable salt or solvate thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compounds of the invention are administered orally.

The invention will now be further illustrated by reference to the following examples. In the examples the Nuclear Magnetic Resonance (NMR) spectra were measured on a Varian Unity Inova 300 or 400 MHz spectrometer and the Mass Spectrometry (MS) spectra measured on a Finnigan Mat SSQ7000 or Micromass Platform spectrometer. Where necessary, the reactions were performed under an inert atmosphere of either nitrogen or argon. Chromatography was generally performed using Matrex Silica 60® (35–70 micron) or Prolabo Silica gel 60® (35–70 micron) suitable for flash silica gel chromatography. High pressure liquid chromatography purification was performed using either a Waters Micromass LCZ with a Waters 600 pump controller, Waters 2487 detector and Gilson FC024 fraction collector or a Waters Delta Prep 4000. The abbreviations m.p. and DMSO used in the examples stand for melting point and dimethyl sulphoxide respectively.

EXAMPLE 1

2-[[2-Amino-5-[(1H-benzimidazol-2-ylmethyl)thio] thiazolo[4,5-d]pyrimidin-7-yl]amino]-2-methyl-1-propanol (a) 6-Amino-1,4-dihydro-2-[(phenylmethyl)thio]-4-oxo-5-thiocyanic acid, pyrimidinyl ester 6-Amino-2-[(phenylmethyl)thio]-4(1H)-pyrimidinone (10.5 g)[preparation as described in WO 9635678] and potassium thiocyanate (25 g) in N,N-dimethylformamide (200 ml) were heated together at 65° C. Pyridine (6.3 ml) was added and the solution cooled to 5° C. Bromine (2.2 ml) was added slowly and the reaction mixture stirred for 2 hours at 5–10° C. The reaction mixture was poured onto ice water, stirred for 1 hour and the solid was isolated by filtration. After washing with water and ether, a pure sample was obtained after tituration with hot methanol.

MS (APCI) 291 (M+H, 100%).

(b) 2-Amino-5-[(phenylmethyl)thio]thiazolo[4,5-d] pyrimidin-7(4H)-one

The product of step a) (7.35 g) was heated at 120° C. in N,N-dimethylformamide (40 ml)/water (10 ml) for 10 hours. After cooling, the resulting solid was filtered off, washed with water, then ethyl acetate to give the subtitle compound.

m.p. ~325° C.

MS (APCI) 291 (M+H, 100%).

(c) 7-Chloro-5-[(phenylmethyl)thio]thiazolo[4,5-d] pyrimidin-2-amine

The product from step (b) (0.89 g), phosphorus oxychloride (12 ml) and N,N-dimethylaniline (1.2 ml) were heated at reflux for 2 hours. The cooled reaction mixture was poured onto ice water and stirred for 2 hours. Chromatography ($SiO_2$, methanol/dichloromethane as eluant) gave the sub-title compound.

m.p. 217–218.5° C.

MS (APCI) 309 (M+H, 100%).

(d) 2-[[2-Amino-5-[(phenylmethyl)thio]thiazolo[4,5-d] pyrimidin-7-yl]amino]-2-methyl-1-propanol The product from step (c) (0.6 g) and 2-amino-2-methylpropanol (1.1 g) in tetrahydrofuran (10 ml) was heated in a sealed vessel at 100° C. for 18 hours. The mixture was evaporated to dryness and purified ($SiO_2$, ethyl acetate as eluant) to give the subtitle compound (0.46 g).

MS (APCI) 362 (M+H$^+$, 100%).

(e) 2-[[2-Amino-5-[(phenylmethyl)sulfonyl]thiazolo[4,5-d] pyrimidin-7-yl]amino]-2-methyl-1-propanol A solution of the product from step (d) (0.65 g) in glacial acetic acid (75 ml) was treated with peracetic acid (36–40% w/w in acetic acid, 0.93 ml) and stirred for 1 hour. The solution was treated with more peracetic acid (3×2 ml) over 40 minutes, and stirred at 70° C. for 1 hour. The excess reagent was destroyed with dimethyl sulphide, and the solution was evaporated. The residue was slurried in toluene and evaporated (3×) to give the subtitled compound, contaminated with a little DMSO

MS: APCI 394 (M+H).

(f) 2-[[2-Amino-5-[(1H-benzimidazol-2-ylmethyl)thio] thiazolo[4,5-d]pyrimidin-7-yl]amino]-2-methyl-1-propanol The product from step (e) was taken up in DMSO (7.5 ml) and treated with potassium t-butoxide (1M in THF, 4.95 ml). An aliquot of the solution (1 ml) was treated with (1H-benzimidazol-2-yl)methanethiol (0.063 g) and stirred at 50° C. for 1 hour. The solution was treated with glacial acetic acid (1 ml) and purified by reverse phase preparative HPLC on Symmetry® C8 column, using, 10 to 60% acetonitrile in 0.1% aqueous ammonium acetate at 20 ml/min over 5 min to give the titled compound (0.013 g)

MS: APCI 402 (M+H). $^1$H NMR: δ (DMSO) 1.32(s, 6H), 3.56 (d, 2H), 4.57 (s, 2H), 4.87 (t, 1H), 6.34 (s, 1H), 7.13 (m, 2H), 7.43–7.52 (m, 2H), 8.01 (s, 2H), 12.33 (s, 1H).

EXAMPLE 2

2-[[2-Amino-5-[(2-furanylmethyl)thio]thiazolo[4,5-d]pyrimidin-7-yl]amino]-2-methyl-1-propanol The titled compound was prepared from furfuryl mercaptan (0.043 g) using the method of example 1, step (f) (0.013 g)

MS: APCI 352 (M+H).

$^1$H NMR: δ (DMSO) 1.33 (s, 6H), 3.55 (d, 2H), 4.38 (s, 2H), 4.87 (t, 1H), 6.30–6.38 (m, 3H), 7.56 (bs, 1H), 8.01 (s, 2H),

EXAMPLE 3

2-[[2-Amino-5-[[1-(2-thienyl)ethyl]thio]thiazolo[4,5-d]pyrimidin-7-yl]amino]-2-methyl-1-propanol The titled compound was prepared from 1-(2-thienyl)ethyl mercaptan (0.055 g) using the method of example 1, step (f) (0.008 g)

MS: APCI 382 (M+H).

$^1$H NMR: δ (DMSO) 1.33 (s, 6H), 1.77 (s, 3H), 3.55 (d, 2H), 4.88 (t, 1H), 5.26 (q, 1H), 6.31 (s, 1H), 6.95–6.97 (m, 1H), 7.90 (d, 1H), 7.40 (dd, 1H), 8.00 (s, 2H),

EXAMPLE 4

(2R)-2-[[2-Amino-5-[[(2-methyl-4-thiazolyl)methyl]thio]thiazolo[4,5-d]pyrimidin-7-yl]amino]-1-propanol (a) (2R)-2-[[2-Amino-5-[(phenylmethyl)thio]thiazolo[4,5-d]pyrimidin-7-yl]amino]-1-propanol Prepared by the method of example 1, step (d), using the product of example 1, step (c) and (R)-(−)-2-amino-1-propanol.

MS (APCI) 348 (M+H$^+$, 100%).

(b) (2R)-2-[(2-Amino-5-mercaptothiazolo[4,5-d]pyrimidin-7-yl)amino]-1-propanol

A stirred solution of the product of step (a) (1 g) in liquid ammonia (20 ml) was treated portionwise with sodium until a permanent blue colour was obtained. The solution was treated with ammonium chloride to dissipate the blue colour, and allowed to evaporate. The residue was taken up in water, filtered and purified by reverse phase preparative HPLC on Xterra® C8 column, using 0 to 20% acetonitrile in water at 20 ml/min over 2 min to give the subtitled compound (0.22 g)

MS: APCI 258 (M+H).

$^1$H NMR: δ (DMSO) 1.09 (d, 3H), 3.39–3.42 (m, obscured by DMSO), 4.05 (bs, 2H), 5.55 (b), 5.99 (b), 7.57 (bs, 2H).

(c) (2R)-2-[[2-Amino-5-[[(2-methyl-4-thiazolyl)methyl]thio]thiazolo[4,5-d]pyrimidin-7-yl]amino]-1-propanol A stirred solution of the product of step (b) (0.05 g) in DMSO (4 ml) was treated with a solution of 4-chloromethyl-2-methylthiazole hydrochloride (0.029 g) and Hunig's base (0.025 g) in NMP (0.5 ml) and stirred for 1 hour. The solution was purified by reverse phase preparative HPLC on Nova-pak® C18 column, using 10 to 60% acetonitrile in 0.1% aqueous ammonium acetate at 50 ml/min over 10 min to give the titled compound (0.021 g)

MS: APCI 369 (M+H).

$^1$H NMR: δ (CD$_3$OD) 1.21 (d, 3H), 2.68 (s, 3H), 3.48–3.64 (mult., 2H), 4.33–4.40 (mult., 1H), 4.46 (s, 2H), 7.31 (s, 1H).

EXAMPLE 5

(2R)-2-[[2-Amino-5-[[(3,5-dimethyl-4-isoxazolyl)methyl]thio]thiazolo[4,5-d]pyrimidin-7-yl]amino]-1-propanol The titled compound was prepared from the product of example 4, step (b), and 3,5-dimethyl-4-chloromethylisoxazole using the method of example 4, step (c) to give a white powder (0.016 g)

MS: APCI 367 (M+H).

EXAMPLE 6

(2R)-2-[[2-Amino-5-[[(5-methyl-2-furanyl)methyl]thio]thiazolo[4,5-d]pyrimidin-7-yl]amino]-1-propanol (a) (2R)-2-[[2-Amino-5-[(phenylmethyl)sulphonyl]thiazolo[4,5-d]pyrimidin-7-yl]amino]-1-propanol.

The product from example 4, step (a), was converted into the subtitled compound by the method of example 1, step (e)

MS: APCI 380 (M+H).

(b) (5-Methylfuran-2-yl)methyl mercaptan

A stirred solution of thiourea (0.18 g) in concentrated hydrochloric acid (0.8 ml) and water (1 ml) was treated with 5-methylfurfuryl alcohol (0.2 g) and stirred for 0.5 h. The mixture was diluted with water to give a clear solution, washed with ether, basified with 10% w/v aqueous sodium hydroxide solution, stirred for 10 min, acidified with concentrated hydrochloric acid and extracted with ether. The washed and dried (MgSO$_4$) extracts were evaporated to give the subtitled compound as a yellow oil that rapidly oxidised to its di-sulphide (0.05 g)

$^1$H NMR: δ (CDCl$_3$) 1.88 (t, 1H), 2.28 (s, 3H), 3.71 (d, 2H), 5.86 (m, 1H), 6.03 (m, 1H).

(c) (2R)-2-[[2-Amino-5-[[(5-methyl-2-furanyl)methyl]thio]thiazolo[4,5-d]pyrimidin-7-yl]amino]-1-propanol.

A solution of the product from step (a) was converted into the titled compound using the product from step (b), and the method of example 1, step (f)

MS: APCI 352 (M+H).

$^1$H NMR: δ (CD$_3$OD) 1.15(d, 3H), 2.13 (s, 3H), 3.42–3.57 (m, 2H), 4.26–4.31(m, 2H), 5.78 (m, 1H), 6.03 (m, 1H).

EXAMPLE 7

N-[4-[[[2-Amino-7-[[(1R)-2-hydroxy-1-methylethyl]amino]thiazolo[4,5-d]pyrimidin-5-yl]thio]methyl]-2-thiazolyl]-acetamide The titled compound was prepared from the product of example 4, step (b), and N-[4-(chloromethyl)-2-thiazolyl]-acetamide, using the method of example 4, step (c)

MS: APCI 412 (M+H).

$^1$H NMR: δ (DMSO) 1.12 (d, 3H), 2.11 (s, 3H), 3.33–3.49 (m, 2H), 4.27 (quin, 1H), 4.40 (s, 2H), 7.01 (s, 1H), 7.58 (bs, 1H), 8.36 (bs, 2H), 12.14 (s, 1H).

EXAMPLE 8

(2R)-2-[[2-Amino-5-[[(5-chloro-1,2,3-thiadiazol-4-yl)methyl]thio]thiazolo[4,5-d]pyrimidin-7-yl]amino]-1-propanol The titled compound was prepared from the product of example 4, step (b), and 5-chloro-4-(chloromethyl)-1,2,3-thiadiazole, using the method of example 4, step (c).

MS: APCI 390 (M+H).

¹H NMR: δ (DMSO) 1.12 (d, 3H), 3.29–3.49 (m, 2H), 4.23 (m, 1H), 4.69 (t, 1H), 4.75 (q, 2H), 7.06 (d, 1H), 8.04 (bs, 2H).

EXAMPLE 9

(2R)-2-[[2-Amino-5-[(5-isoxazolylmethyl)thio]thiazolo[4,5-d]pyrimidin-7-yl]amino]-1-propanol The titled compound was prepared from the product of example 4, step (b), and bromomethylisoxazole, using the method of example 4, step (c).

Mp 183–5C.

MS: APCI 339 (M+H, 100%).

¹H NMR: δ (DMSO) 1.10 (d, 3H), 1.87 (s, 1H), 3.32–3.44 (m, 2H+H₂O), 4.17 (m, 1H), 4.49 (s, 2H), 6.36, (s, 1H), 7.06 (d, 1H), 8.03 (bs, 2H), 8.44 (s, 1H).

EXAMPLE 10

2-[[2-Amino-5-[[(2-methyl-4-thiazolyl)methyl]thio]thiazolo[4,5-d]pyrimidin-7-yl]amino]-1,3-propanediol a) 6-Amino-2-[[(2-methyl-4-thiazolyl)methyl]thio]-4(3H)-pyrimidinone 4-Amino-6-hydroxy-2-mercaptopyrimidine monohydrate (0,161 g) and sodium hydroxide (0.08 g) were stirred in dry DMF (4 ml) for 20 mins. 4-Chloromethyl, 2-methylthiazole hydrochloride hydrate (0.2 g) was added and the mixture stirred for 3 hr then poured onto water (150 ml) to give a solution. The subtitled product crystallised and was collected, washed with water and dried (0.2 g).

MS: ES+255 (M+H, 100%).

¹H NMR: δ (DMSO) 2.53 (s, 3H), 4.36 (s, 2H), 4.94 (s, 1H), 6.55 (bs, 2H), 7.44 (s, 1H), 11.46 (bs, 1H).

b) 2-Amino-5-[[(2-methyl-4-thiazolyl)methyl]thio]-thiazolo[4,5-d]pyrimidin-7(6H)-one The product from step (a) (24.3 g) was stirred in dry DMF (400 ml) with pyridine (13.1 ml) and potassium thiocyanate (37.1 g) at 0C. Bromine (4.5 ml) was added over 1 hr and the mixture kept at 0C for a further 2 hrs. The mixture was poured onto water to give a solution which was then evaporated to low volume. Water was added to give a precipitate which was collected. The solid was dissolved in dilute hydrochloric acid and reprecipitated by the addition of sodium bicarbonate solution. The solid was collected, washed with water and dried to afford the sub-title compound (8.7 g)

MS. ES+ve 312 (M+H, 100%).

¹H NMR: δ (DMSO) 2.62 (s, 3H), 4.41 (s, 2H), 7.57 (s, 1H), 7.70 (bs, 2H), 12.37 (bs, 1H).

c) 7-Chloro-5-[[(2-methyl-4-thiazolyl)methyl]thio]-thiazolo[4,5-d]pyrimidin-2-amine The product from step (b), (8.7 g), was suspended in phosphorus oxychloride (88 ml) and dimethylaniline (8.8 ml). The mixture was heated under reflux for 2 hrs then evaporated. The residue was stirred in hot water, cooled and the pH adjusted with sodium hydroxide solution to pH5. The solid was collected, washed with water and dried. Chromatography (SiO₂, methanol/dichloromethane as eluant) gave the sub-title compound (4.3 g)

MS. APCI+ve 330/332 (M+H), 330 (100%).

¹H NMR: δ (DMSO) 2.63 (s, 3H), 4.44 (s, 2H), 7.36 (s, 1H), 8.96 (bs, 2H).

d) 2-[[2-Amino-5-[[(2-methyl-4-thiazolyl)methyl]thio]thiazolo[4,5-d]pyrimidin-7-yl]amino]-1,3-propanediol The product from step (c) (0.99 g) and 2-amino-1,3-propanediol (0.55 g), were stirred in dry NMP (10 ml) with hunigs base (1.75 ml) at 100° C. for 20hrs. The mixture was poured onto water and evaporated. Water was added and the solid collected, washed with water and dried. A sample (0.11 g) was purified by reverse phase preparative HPLC on Nova-pak® C18 column, using acetonitrile in 0.1% aqueous ammonium acetate gave the titled compound (0.04 g)

Mp 158–160C.

MS: APCI+ve 385 (M+H, 100%).

¹H NMR: δ (DMSO) 2.62 (s, 3H), 3.51 (m, 4H), 4.18 (m, 1H), 4.37 (s, 2H), 4.64 (t, 2H), 6.87, (d, 1H), 7.31 (s, 1H), 8.00 (bs, 2H).

EXAMPLE 11

2-[[2-Amino-5-[[(2-methyl-4-thiazolyl)methyl]thio]thiazolo[4,5-d]pyrimidin-7-yl]amino]-2-methyl-1-propanol The titled compound was prepared from the product of example 10, step (c) and 2-amino,2-methylpropanol (0.54 g) using the method of example 10, step (d).

Mp 250–252C.

MS: APCI+ve 383 (M+H, 100%).

¹H NMR: δ (DMSO) 1.32 (s, 6H), 2.62 (s, 3H), 3.55 (d, 2H), 4.38 (s, 2H), 4.86 (t, 1H), 6.30 (s, 1H), 7.30, (s, 1H), 8.00 (bs, 2H).

EXAMPLE 12

(2R)-2-[[2-Amino-5-[(2-furanylmethyl)thio]thiazolo[4,5-d]pyrimidin-7-yl]amino]-1-propanol The titled compound was prepared from the product of example 1, step (e) and furfuryl mercaptan (0.15 ul) using the method of example 1, step (i) (0.024 g)

Mp 145–150C.

MS: APCI 338 (M+H, 100%).

¹H NMR: δ (DMSO) 1.13 (d, 3H), 3.32–3.47 (m, 2H+H₂O), 4.21 (m, 1H), 4.41 (bs, 2H), 4.71 (t, 1H), 6.29 (m, 1H), 6.36 (m, 1H), 7.01 (d, 1H), 7.55 (m, 1H), 8.53 (bs, 2H).

Pharmacological Data

Ligand Binding Assay

[$^{125}$I]IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp16283–16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 μg/ml soybean trypsin inhibitor, 3 mM benzamidine, 0.5 μg/ml leupeptin and 100 μg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM NaH₂PO₄), 0.1% (w/v) gelatin and 10% (v/v) glycerol.

All assays were performed in a 96-well MultiScreen 0.45 μm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM CaCl$_2$, 1 mM MgCl$_2$, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compounds of formula (I) according to the Examples were found to have IC$_{50}$ values of less than (<) 10 μM.

Intracellular Calcium Mobilisation Assay

Human neutrophils were prepared from EDTA-treated peripheral blood, as previously described (Baly et al. (1997) Methods in Enzymology 287 pp70–72), in storage buffer [Tyrode's salt solution (137 mM NaCl, 2.7 mM KCl, 0.4 mM NaH$_2$PO$_4$) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp513–519). Cells were Loaded for 1 hour at 37° C. in loading buffer (storage buffer with 0.1% (w/v) gelatin) containing 5 μM fluo-3 AM ester, washed with loading buffer and then resuspended in Tyrode's salt solution supplemented with 5.7 mM glucose, 0.1% (w/v) bovine serum albumin (BSA), 1.8 mM CaCl$_2$ and 1 mM MgCl$_2$. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an A$_{50}$ concentration of GROα and the transient increase in fluo-3 fluorescence ($\lambda_{Ex}$=490 nm and $\lambda_{Em}$=520 nm) monitored using a FLIPR (Fluorometric Imaging Plate Reader, Molecular Devices, Sunnyvale, U.S.A.).

The compounds of formula (I) according to the Examples were tested and found to be antagonists of the CXCR2 receptor in human neutrophils.

What is claimed is:

1. A compound of formula (I) or a pharmaceutically acceptable salt thereof:

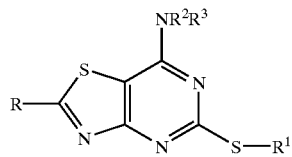

(I)

wherein R represents a hydrogen atom, or a group —NR$^4$R$^5$;

R$^4$ and R$^5$ each independently represent a hydrogen atom, or a 4-piperidinyl, C$_3$–C$_6$ cycloalkyl or C$_1$–C$_8$ alkyl group, which latter two groups may be optionally substituted by one or more substituent groups independently selected from halogen atoms and —NR$^6$R$^7$, —CONR$^6$R$^7$, —OR$^8$, —COOR$^8$, —NR$^9$COR$^{10}$, —SR$^{11}$, —SO$_2$R$^{11}$, —SO$_2$NR$^6$R$^7$, —NR$^9$SO$_2$R$^{10}$, morpholinyl, C$_1$–C$_4$ alkyl, C$_3$–C$_6$ cycloalkyl, tetrahydrofuranyl aryl and heteroaryl groups, the aryl and heteroaryl groups being optionally substituted by one or more substituents independently selected from halogen atoms and cyano, nitro, —NR$^6$R$^7$, —CONR$^6$R$^7$, —OR$^8$, —NR$^9$COR$^{10}$, —SO$_2$NR$^6$R$^7$, —NR$^9$SO$_2$R$^{10}$, C$_1$–C$_6$ alkyl and trifluoromethyl groups, or R$^4$ and R$^5$ together with the nitrogen atom to which they are attached form a 4- to 7-membered saturated heterocyclic ring system, which ring system may be optionally substituted by one or more substituent groups independently selected from:

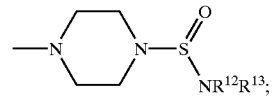

—NR$^6$R$^7$, —CONR$^6$R$^7$, —OR$^8$, —COOR$^8$, —NR$^9$COR$^{10}$, and C$_1$–C$_6$ alkyl optionally substituted by one or more substituents independently selected from halogen atoms and —NR$^{11}$R$^{12}$ and —OR$^8$ groups, R$^1$ represents a C$_1$–C$_8$ alkyl group substituted by a five-membered heterocycle;

R$^2$ and R$^3$ each independently represent a hydrogen atom, or a C$_3$–C$_7$ carbocyclic, C$_1$–C$_8$ alkyl, C$_2$–C$_6$ alkenyl or C$_2$–C$_6$ alkynyl group, the latter four groups may be optionally substituted by one or more substituent groups independently selected from: halogen atoms, —NR$^6$R$^7$, —CONR$^6$R$^7$, —OR$^8$, —COOR$^8$, —NR$^9$COR$^{10}$, —SR$^{11}$, —SO$_2$R$^{11}$, —SO$_2$NR$^6$R$^7$, —NR$^9$SO$_2$R$^{10}$ or a 3–8 membered ring optionally containing one or more atoms selected from O, S, NR$^9$ and itself optionally substituted by C$_{1-3}$-alkyl, halogen, R$^8$ represents hydrogen, C$_1$–C$_6$ alkyl or a phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ R$^6$ and R$^7$ independently represent a hydrogen atom or a C$_1$–C$_6$ alkyl or phenyl group the latter two of which may be optionally substituted by one or more substituent groups independently selected from halogen atoms, phenyl, —OR$^{14}$ and —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or R$^6$ and R$^7$ together with the nitrogen atom to which they are attached form a 4- to 7-membered saturated heterocyclic ring system optionally comprising a further heteroatom selected from oxygen and nitrogen atoms, which ring system may be optionally substituted by one or more substituent groups independently selected from phenyl, —OR$^{14}$, —COOR$^{14}$, —NR$^{15}$R$^{16}$, —CONR$^{15}$R$^{16}$, —NR$^{15}$COR$^{16}$, —SO$_2$NR$^{15}$R$^{16}$, NR$^{15}$SO$_2$R$^{16}$ or C$_1$–C$_6$ alkyl, itself optionally substituted by one or more substituents independently selected from halogen atoms and —NR$^{15}$R$^{16}$ and —OR$^7$ groups, R$^{11}$ represents a hydrogen atom or a C$_1$–C$_6$, or phenyl group, each of which may be optionally substituted by one or more substituent groups independently selected from halogen atoms, phenyl, —OR$^{17}$ and —NR$^{15}$R$^{16}$, and R$^9$, R$^{10}$, R$^{12}$, R$^{13}$, R$^{14}$, R$^{15}$, R$^{16}$, and R$^{17}$ independently represent a hydrogen atom or a C$_1$–C$_6$, alkyl, or a phenyl group.

2. A compound according to claim 1, wherein R represents a group —NR$^4$R$^5$.

3. A compound according to claim 1 wherein R$^4$ and R$^5$ each represent a hydrogen atom.

4. A compound according to claim 1, wherein R$^1$ represents a methyl group substituted by a furan or thiazole.

5. A compound according to claim 1, wherein one of R$^2$ and R$^3$ is hydrogen and the other is C$_1$–C$_8$ alkyl substituted by hydroxy and one or more methyl or ethyl groups.

6. A compound according to claim 1 being selected from:

2-[[2-Amino-5-[(1H-benzimidazol-2-ylmethyl)thio]thiazolo[4,5-d]pyrimidin-7-yl]amino]-2-methyl-1-propanol;

2-[[2-Amino-5-[(2-furanylmethyl)thio]thiazolo[4,5-d]pyrimidin-7-yl]amino]-2-methyl-1propanol 2-[[2-Amino-5-[[1-(2-thienyl)ethyl]thio]thiazolo[4,5-d]pyrimidin-7-yl]amino]-2-methyl-1-propanol (2R)-2-[[2-amino-5-[[(2-methyl-4-thiazolyl)methyl]thio]thiazolo[4,5-d]pyrimidin-7-yl]amino]-1-propanol (2R)-2-[[2-Amino-5-[[(3,5-dimethyl-4-isoxazolyl)methyl]thio]thiazolo[4,5-d]pyrimidin-7-yl]amino]-1-propanol (2R)-2-[[2-Amino-5-[[(5-methyl-2-furanyl)methyl]thio]thiazolo[4,5-d]pyrimidin-7-yl]amino]-1-propanol N-[4-[[[2-Amino-7-[[(1R)-2-hydroxy-1-methylethyl]amino]thiazolo[4,5-d]pyrimidin-5-yl]thio]methyl]-2-thiazolyl]-acetamide;

(2R)-2-[[2-Amino-5-[[(5-chloro-1,2,3-thiadiazol-4-yl)methyl]thio]thiazolo[4,5-d]pyrimidin-7-yl]amino]-1-propanol (2R)-2-[[2-Amino-5-[(5-isoxazolylmethyl)thio]thiazolo[4,5-d]pyrimidin-7-yl]amino]-1-propanol 2-[[2-Amino-5-[[(2-methyl-4-thiazolyl)methyl]thio]thiazolo[4,5-d]pyrimidin-7-yl]amino]-1,3-propanediol 2-[[2-Amino-5-[[(2-methyl-4-thiazolyl)methyl]thio]thiazolo[4,5-d]pyrimidin-7-yl]amino]-2-methyl-1-propanol (2R)-2-[[2-Amino-5-[(2-furanylmethyl)thio]thiazolo[4,5-d]pyrimidin-7-yl]amino]-1-propanol and their pharmaceutically acceptable salts and solvates.

7. A pharmaceutical composition comprising a compound of formula (I), or a pharmnaceutically acceptable salt thereof, as claimed in claim 1 in association with a pharmaceutically acceptable adjuvant, diluent or carrier.

8. A process for the preparation of a compound of formula (I) as defined in claim 1 which comprises:

a) treatment of a compound of formula (II):

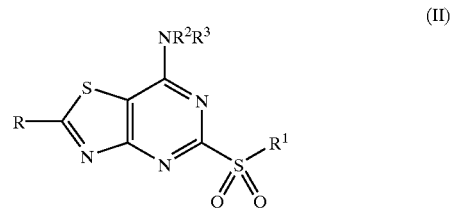

(II)

where R, R$^1$, R$^2$ and R$^3$ are as defined in formula (I) or are protected derivatives thereof with a thiol R$^1$SH in the presence of a base, or (b) treatment of a compound of formula (III):

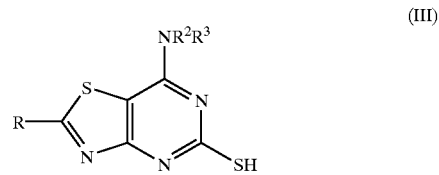

(III)

where R, R$^2$ and R$^3$ are as defined in formula (I) or are protected derivatives thereof with a compound of formula R$^1$X where R$^1$ is as defined in formula (I) and X is a leaving group, and optionally after (a) or (b):

removing any protecting groups;

forming a pharmaceutically acceptable salt.

* * * * *